US006953602B2

(12) United States Patent
Carte et al.

(10) Patent No.: US 6,953,602 B2
(45) Date of Patent: Oct. 11, 2005

(54) PATTERN COATED ADHESIVE ARTICLE

(75) Inventors: Theresa L. Carte, Euclid, OH (US); Kim Vesey, Hillsborough, NJ (US); Omar Attia, Lake View, NY (US); Brett Ulrich, South Wales, NY (US); Karen L. Spilizewski, Euclid, OH (US); Robert Li-Jiun Sun, Succasunna, NJ (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/271,164

(22) Filed: Oct. 15, 2002

(65) Prior Publication Data

US 2003/0064190 A1 Apr. 3, 2003

Related U.S. Application Data

(62) Division of application No. 09/643,616, filed on Aug. 22, 2000, now Pat. No. 6,495,229.
(60) Provisional application No. 60/154,583, filed on Sep. 17, 1999.

(51) Int. Cl.$^7$ .............................................. A41F 13/00
(52) U.S. Cl. .................. 427/208.4; 427/2.1; 427/2.31; 427/208.6; 602/41; 602/54; 602/55; 602/57
(58) Field of Search ............................. 427/208.4, 2.1, 427/2.31, 208.6; 602/41, 54, 55, 57

(56) References Cited

U.S. PATENT DOCUMENTS

| | | | |
|---|---|---|---|
| 2,940,868 A | 6/1960 | Patchell | 117/38 |
| 3,039,893 A | 6/1962 | Banigan, Jr. et al. | 117/122 |
| 3,073,304 A | 1/1963 | Schaar | 128/156 |
| 3,121,021 A | 2/1964 | Copeland | 117/122 |
| 3,364,063 A | 1/1968 | Satas | 117/98 |
| 3,645,835 A | 2/1972 | Hodgson | 161/146 |
| 4,080,348 A | 3/1978 | Korpman | 260/27 |
| 4,163,822 A | 8/1979 | Walter | 428/304 |
| 4,418,822 A | 12/1983 | Dotta | 206/441 |
| 4,551,490 A | 11/1985 | Doyle et al. | 524/22 |
| 4,595,001 A | 6/1986 | Potter et al. | 128/156 |
| 4,629,457 A | 12/1986 | Ness | 604/382 |
| 4,645,502 A | 2/1987 | Gale et al. | 604/896 |
| 4,711,781 A | 12/1987 | Nick et al. | 424/446 |
| 4,743,249 A | 5/1988 | Loveland | 424/447 |
| 4,747,401 A | 5/1988 | Potter et al. | 128/156 |
| 4,753,840 A | 6/1988 | Van Gompel | 428/171 |
| 4,761,324 A | 8/1988 | Rautenberg et al. | 428/198 |
| 4,773,408 A | 9/1988 | Cilento et al. | 128/156 |
| 4,773,409 A | 9/1988 | Cilento et al. | 128/156 |
| 4,784,856 A | 11/1988 | Fukuda et al. | 424/448 |
| 4,797,171 A | 1/1989 | Van Gompel | 156/322 |
| 4,798,201 A | 1/1989 | Rawlings et al. | 128/156 |
| 4,879,178 A | 11/1989 | Sun et al. | 428/355 |
| 4,883,668 A | 11/1989 | Ohta | 424/448 |

(Continued)

FOREIGN PATENT DOCUMENTS

| | | | |
|---|---|---|---|
| CA | 2045247 | * | 4/1992 |
| CN | 2021308 | | 2/1991 |

(Continued)

*Primary Examiner*—Nasser Ahmad
(74) *Attorney, Agent, or Firm*—Renner, Otto, Boisselle & Sklar, LLP

(57) ABSTRACT

The invention relates to a adhesive article comprising at least one backing layer with a first and second surface and a pressure sensitive adhesive layer adhered first surface of the backing layer in a pattern, wherein the pattern of the adhesive layer has an adhesive free area of less than about 25% and wherein the adhesive article has a water vapor transmission rate of greater than about 2000 g/m$^2$/24 hour. The invention also relates to a method of forming an adhesive article comprising (a) providing a release liner, (b) applying pressure sensitive adhesive in a pattern wherein the free adhesive area is less than 25%, and (c) applying a backing layer to the pressure sensitive adhesive.

20 Claims, 2 Drawing Sheets

U.S. PATENT DOCUMENTS

| | | | |
|---|---|---|---|
| 4,911,916 A | 3/1990 | Cleary | 424/449 |
| 4,935,287 A | 6/1990 | Johnson et al. | 428/198 |
| 4,944,958 A | 7/1990 | Langen et al. | 427/2 |
| RE33,353 E | 9/1990 | Heinecke | 428/40 |
| 4,984,566 A | 1/1991 | Sekine et al. | 128/90 |
| 4,995,382 A | 2/1991 | Lang et al. | 128/156 |
| 5,000,172 A | 3/1991 | Ward | 128/155 |
| 5,009,224 A | 4/1991 | Cole | 128/156 |
| 5,012,801 A | 5/1991 | Feret | 128/155 |
| 5,099,832 A | 3/1992 | Ward | 602/57 |
| 5,106,629 A | 4/1992 | Cartmell et al. | 424/445 |
| 5,133,972 A | 7/1992 | Ferrini et al. | 424/449 |
| 5,147,338 A | 9/1992 | Lang et al. | 604/304 |
| 5,147,339 A | 9/1992 | Sundstrom | 604/307 |
| 5,147,698 A | 9/1992 | Cole | 428/40 |
| 5,156,589 A | 10/1992 | Langen et al. | 602/77 |
| 5,175,052 A | 12/1992 | Tokuda et al. | 428/355 |
| 5,188,124 A | 2/1993 | Feret | 128/889 |
| 5,200,190 A | 4/1993 | Azuma et al. | 424/443 |
| 5,244,457 A | 9/1993 | Karami et al. | 602/55 |
| 5,244,677 A | 9/1993 | Kreckel et al. | 424/448 |
| 5,262,165 A | 11/1993 | Govil et al. | 424/448 |
| 5,276,079 A | 1/1994 | Duan et al. | 524/386 |
| 5,322,695 A | 6/1994 | Shah et al. | 424/448 |
| 5,338,490 A | 8/1994 | Dietz et al. | 252/500 |
| 5,389,376 A | 2/1995 | Duan et al. | 424/448 |
| 5,407,713 A | 4/1995 | Wilfong et al. | 428/34.1 |
| 5,409,472 A | 4/1995 | Rawlings et al. | 604/307 |
| 5,413,567 A | 5/1995 | Barth et al. | 604/307 |
| 5,489,624 A | 2/1996 | Kantner et al. | 524/376 |
| 5,589,249 A | 12/1996 | Bodford et al. | 428/200 |
| 5,613,942 A | 3/1997 | Lucast et al. | 602/52 |
| 5,614,050 A | 3/1997 | Carsten et al. | 156/231 |
| 5,622,711 A | 4/1997 | Chen | 424/445 |
| 5,633,010 A | 5/1997 | Chen | 424/448 |
| 5,641,506 A * | 6/1997 | Talke et al. | 424/443 |
| 5,653,699 A | 8/1997 | Reed et al. | 604/307 |
| 5,660,178 A | 8/1997 | Kantner et al. | 128/640 |
| 5,670,557 A | 9/1997 | Dietz et al. | 522/184 |
| 5,681,579 A * | 10/1997 | Freeman | 424/448 |
| 5,783,209 A | 7/1998 | Imamura et al. | 424/448 |
| 5,785,985 A | 7/1998 | Czech et al. | 424/448 |
| 5,810,756 A | 9/1998 | Montecalvo et al. | 602/59 |
| 5,811,116 A | 9/1998 | Gilman et al. | 424/443 |
| 5,814,032 A | 9/1998 | Hori et al. | 604/307 |
| 5,827,528 A | 10/1998 | Kubo et al. | 424/443 |
| 5,840,327 A | 11/1998 | Gale et al. | 424/448 |
| 5,846,558 A | 12/1998 | Nielsen et al. | 424/448 |
| 5,853,750 A | 12/1998 | Dietz et al. | 424/448 |
| 5,891,077 A | 4/1999 | Gilman et al. | 602/57 |
| 5,928,972 A | 7/1999 | Mashiko et al. | 442/334 |
| 6,051,747 A | 4/2000 | Lindqvist et al. | 602/46 |
| 6,180,544 B1 | 1/2001 | Jauchen et al. | 442/150 |
| 6,383,630 B1 | 5/2002 | Jauchen et al. | 428/343 |

FOREIGN PATENT DOCUMENTS

| | | |
|---|---|---|
| DE | 35 39 533 A1 | 5/1987 |
| DE | 196 28 268 A1 | 1/1998 |
| DE | 196 28 294 A1 | 1/1998 |
| EP | 0 136 393 | 2/1984 |
| EP | 0 353 972 A1 | 2/1990 |
| EP | 0 452 368 A1 | 10/1991 |
| EP | 0 539 032 A1 | 4/1993 |
| GB | 713838 | 8/1954 |
| GB | 1 570 669 | 2/1980 |
| GB | 2 224 445 A | 5/1990 |
| JP | 7-275290 | 10/1995 |
| JP | 8-217668 | 8/1996 |
| WO | 97/07759 | 3/1997 |
| WO | 97/42922 | 11/1997 |
| WO | 97/42944 | 11/1997 |
| WO | 98/25999 | 6/1998 |

* cited by examiner

PATTERN COATED ADHESIVE ARTICLE

REFERENCE TO RELATED APPLICATION

This application claims priority of provisional patent application Ser. No. 60/154,583, filed Sep. 17, 1999, and is a divisional of U.S. application Ser. No. 09/643,616, filed Aug. 22, 2000 now U.S. Pat. No. 6,495,229.

TECHNICAL FIELD

This invention relates to a highly breathable pressure sensitive adhesive article, such as a bandage or tape. More particularly, the invention relates to a pressure sensitive adhesive article having both good adhesion and high moisture vapor transmission rate characteristics. In one embodiment, the adhesive article has a backing layer and a rubber based pressure sensitive adhesive.

BACKGROUND OF THE INVENTION

Adhesive articles, such as bandages and tapes, are well known in the art and are commonly used as first aid wound dressings and other medical applications. Conventional adhesive bandages contain a central pad area (padstock) surrounded by adhesive areas. Particularly, adhesive bandages or tapes generally contain an elongated strip of cloth or plastic backing layer which has a pressure sensitive adhesive coated on one surface. A gauze or sponge pad is secured to the adhesive surface in a central location thereby serving as a wound covering material. The wound facing surface of the pad may be plastic coated or otherwise treated to prevent the padstock from adhering to the wound. Release strips are placed over the adhesive areas and typically the wound covering padstock and the entire assembly is enclosed in a sealed package and sterilized so as to be ready for use.

A disadvantage of adhesive articles in medical application is maceration. Normal human skin releases about 500 g/m$^2$/24 hours of water in a resting state. When the water released by the skin is unable to evaporate then the skin becomes white in color and prune-like in appearance. After some time, the integrity of the skin could be weakened. Also the time for healing is the wound is often extended.

Rubber based pressure sensitive adhesives have the advantages of high adhesion and relatively low cost. The high adhesion is achieved without application of significant amounts of pressure. However, rubber based adhesives can be disadvantageous because they have inherently low breathability (i.e. low moisture vapor transmission rate (MVTR)). Therefore, such disadvantageous properties make rubber based adhesives generally unsuitable for skin contacting bandage applications.

U.S. Pat. No. 5,244,457 relates to a vented wound dressing made of a thin vapor-permeable sheet material having a pressure sensitive adhesive coating, the coating having repeating adhesive free areas. The adhesive covers at least 50% of the surface area of the thin vapor-permeable sheet material.

U.S. Pat. No. 5,641,506 relates to a medical patch material made of a support coated with a pressure sensitive hot melt adhesive coating using the gravure printing method. The medical patch material requires an adhesive-free area of at least 30% (between 30% and 60%), an adhesive coat weight between 30 and 160 g/m$^2$, and a block copolymer adhesive having certain properties to achieve an MVTR of at least 2,000 g/m$^2$/24 hours.

Canadian Patent 2,045,247 relates to a wound dressing made of a thin film carrying a discontinuous coating of a pressure sensitive adhesive, such as a rubber-based pressure sensitive adhesive, in such a manner so as to define adhesive-free areas. The film has an MVTR of at least 50 g/m$^2$/24 hours, and preferably 500 g/m$^2$/24 hours.

SUMMARY OF THE INVENTION

The invention relates to an adhesive article comprising at least one backing layer with a first and second surface and a pressure sensitive adhesive layer adhered to the first surface of the backing layer in a pattern, wherein the pattern of the adhesive layer has an adhesive-free area of less than about 25% and wherein the adhesive article has a water vapor transmission rate of greater than about 2000 g/m$^2$/24 hour. The invention also relates to a method of forming an adhesive article comprising (a) providing a release liner, (b) applying pressure sensitive adhesive in a pattern wherein the free adhesive area is less than 25%, and (c) applying a backing layer to the pressure sensitive adhesive.

The present invention provides for an adhesive article that strongly adheres to human skin while permitting water vapor transmission there through; thus, not causing or exacerbating wound and skin problems. Accordingly the present invention also provides methods of facilitating the healing of wounds using the adhesive article. The present invention achieves MVTR values of greater than about 2000 g/m$^2$/24 hours with adhesive-free areas of less than about 25%. Not only is high breathability achieved, but also the high level of adhesive coverage allows for improved adhesion to skin due to greater surface contact between adhesive and skin.

This invention relates to a highly breathable pressure sensitive adhesive bandage that is manufactured using pattern coating of an inexpensive, non-breathable pressure sensitive adhesive. High breathability, as measured by moisture vapor transmission rate (MVTR), is desirable features of an adhesive bandage in order to prevent maceration of the skin due to trapped moisture, and to enhance comfort during wear of the bandage by the end user.

DETAILED DESCRIPTION OF THE INVENTION

Figure 1:
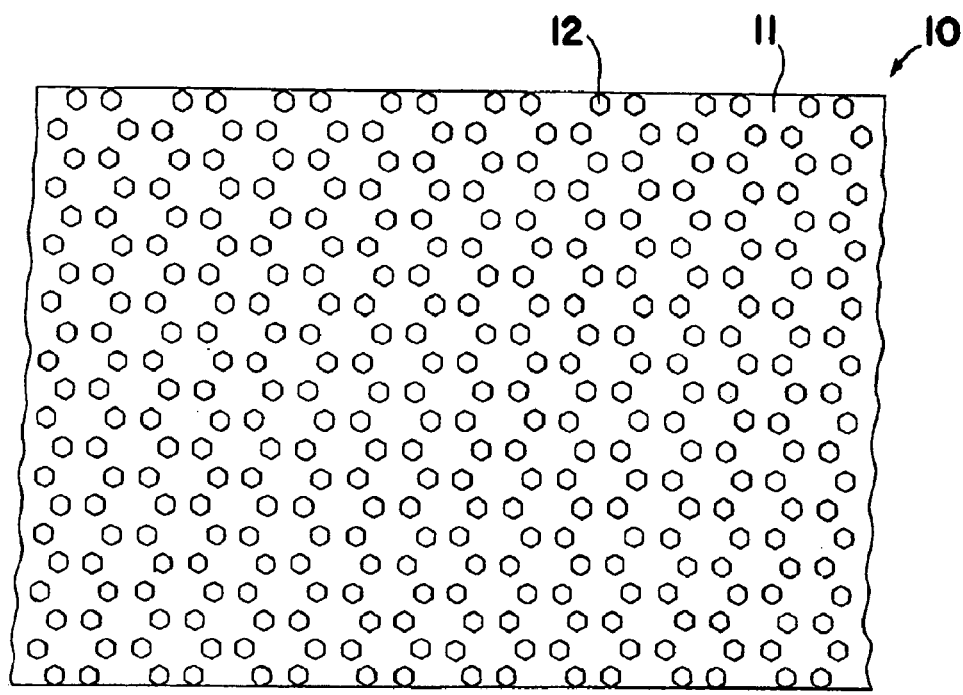
FIG. 1 is a top view of the backing layer and the patterned adhesive.

As discussed above the adhesive articles are useful as medical bandages and/or medical tapes. The articles have a moisture vapor transmission rate of at least about 2000 g/m$^2$/24 hour. In one embodiment, the moisture vapor transmission rate is at least about 2500 g/m$^2$/24 hour. In another embodiment, the moisture vapor transmission rate is at least about 3000 g/m$^2$/24 hour, and in yet another embodiment, at least about 5000 g/m$^2$/24 hour. The present articles even have vapor transmission rates of 7,000 g/m$^2$/24 hour or higher. The water vapor transmission rate is determined by ASTM F-1249-90.

The articles also have an adhesive-free area of less than about 25%. In one embodiment, the adhesive-free area is in the range of about 5% to about 25%. In another embodiment, the adhesive-free area is in the range of about 7% to about 20%, and in another embodiment, in the range of about 8% to about 17%. In yet another embodiment, the adhesive-free area is in the range of about 10% to about 15%. Here and elsewhere in the claims and specification, the range and ratio limits may be combined.

The adhesive-free area is determined by actual measurement of the areas of the backing layer that are free of adhesive. It is recognized that the adhesive can flow some during application. The term []adhesive-free[] refers to the part of the article which is the exposed backing layer without adhesive. The adhesive-free area is determined by using an Olympus SZH zoom stereo telescope and Image-Pro Plus software. A Pulnix video camera, and television monitor are used to capture the image and the software is used to measure the part of the backing area without adhesive. The area of the backing layer that is adhesive-free is divided by the total area of the backing layer sample and multiplied by 100 to yield the adhesive-free area of the sample.

The adhesive articles according to the present invention contain a backing layer having a first and second side. An adhesive is adhered to the first side of the backing layer in a pattern. To achieve high MVTR, the adhesive is applied to the film backing in a discontinuous pattern so that there are adhesive coated areas and adhesive-free areas. The adhesive coated areas allow for adhesion of the bandage to the skin, while the adhesive-free areas allow moisture vapor to pass through, thereby simultaneously achieving high breathability and good wear performance using relatively low cost materials.

The backing layer material may be any suitable polymeric film, plastic foam (including open celled foam), a woven fabric, knitted fabric or a non-woven fabric. The fabrics may be natural or synthetic materials. The backing layer possesses at least some breathability.

In one embodiment, a porous backing layer is employed. For example, in one embodiment, the backing layer is an apertured polymeric film, such as polyolefin film, a nonwoven, cloth fabric, or the like. It is noted that the discontinuous adhesive pattern according to the invention also enhances the breathability of products that do not have porous backings, as long as the backing itself has some inherent breathability, such as in the case with polyurethane films. When an apertured film or foam is used, a plurality of apertures aligns with the adhesive free areas. In one embodiment, there are from about 2 to about 15 apertures per each adhesive-free area. In another embodiment, there are about 3 to about 8, or from 4 to about 6 apertures per each adhesive-free area.

Examples of materials suitable for use as a backing layer or strip include polyolefins, such as polyethylene, polypropylene, ethylene propylene copolymers, and ethylene butylene copolymers, polyurethanes, polyurethane foams, polystyrenes, plasticized polyvinylchlorides, polyesters, polyamides, and cotton. The plastic film may be in the form of a sheet or foam strip. Specific examples include Platilon UO4, which is a polyurethane film having a thickness of about 25 micron manufactured by Atochem. Another useful and preferred backing layer is a 3.3. mil apertured polyolefin film, available commercially from Tredegar Film Products under the trade name X6989.

The backing layer is preferably flexible yet resistant to tearing. In one embodiment, the thickness of the backing layer of the adhesive article of the present invention is from about 0.1 mil to about 50 mils. In another embodiment, the thickness of the backing layer is from about 0.5 mil to about 20. In another embodiment, the thickness of the backing layer is from about 0.7 mil to about 10 mils. In yet another embodiment, the thickness of the backing layer is from about 1 mil to about 5 mils.

The backing layer may be opaque or translucent. Normally it has a skin color, but "designer" colors and patterns, as well as cartoon character designs, are becoming popular. It may be solid or porous, permeable or perforated, as adapted for the requirements of the product application, as well as being a function of the composition and form of the backing material. In one embodiment, the adhesive article is pigmented and reduces the visibility of the pattern coating.

In one embodiment, the backing layer is substantially impervious to liquid, especially wound exudate. In yet another embodiment, the backing layer is substantially impervious to bacteria. In another embodiment, the backing layer is capable of absorbing liquid, especially wound exudate. In another embodiment, perforations or small apertures in the backing layer facilitate high breathability.

The adhesive of the present invention forms a pattern on the backing layer. The adhesive may be applied in any number of patterns. For example, one potential pattern would be a sine wave using either a smooth pattern (rounded waves) or a sharp pattern (triangle shaped waves) closely packed together. In a preferred embodiment, the adhesive forms a continuous network so that the adhesive-free areas are not interconnected. In this embodiment, moisture is substantially prevented from seeping into and under the bandage through adhesive free channels at the edges of the bandage during wear. Additionally, adhesive article is less likely to fall off from the adverse affects of moisture. Moreover, this embodiment minimizes having adhesive-free areas around the edge of the bandage that could decrease adhesion performance by creating a site for edge lift. The adhesive layer is typically present in coat weight from about 10 to about 80, or from about 15 to about 70, or from about 20 to 60 grams per square meter (gsm).

For example, one specific embodiment of a preferred adhesive pattern would be that of a "honeycomb" design. The "honeycomb" design may be achieved in any suitable manner using various adhesive-free shapes in various configurations. For example, the adhesive-free areas are in the form of circular dots, hexagonal dots, square dots, or any geometrical shape. These dots are configured so that they line up in rows or are offset between rows. In a preferred embodiment, the hexagonal dot that is offset between rows tends to achieve the desired balance between adhesion coverage and adhesive-free areas.

The adhesive article may be further described by reference to the accompanying drawings. FIG. 1 has adhesive article 10 with the backing layer containing adhesive layer 11 and adhesive free area 12. The pattern may by prepared by any means know to those in the art. The pattern could be formed by spraying the pressure sensitive adhesive or by melt blowing the pressure sensitive adhesive. The pattern could be formed by printing the adhesive. The printing may be any means that can form the pattern. Examples of useful printing means include gravure, lithographic, screen, or flexographic printing.

Figure 2:
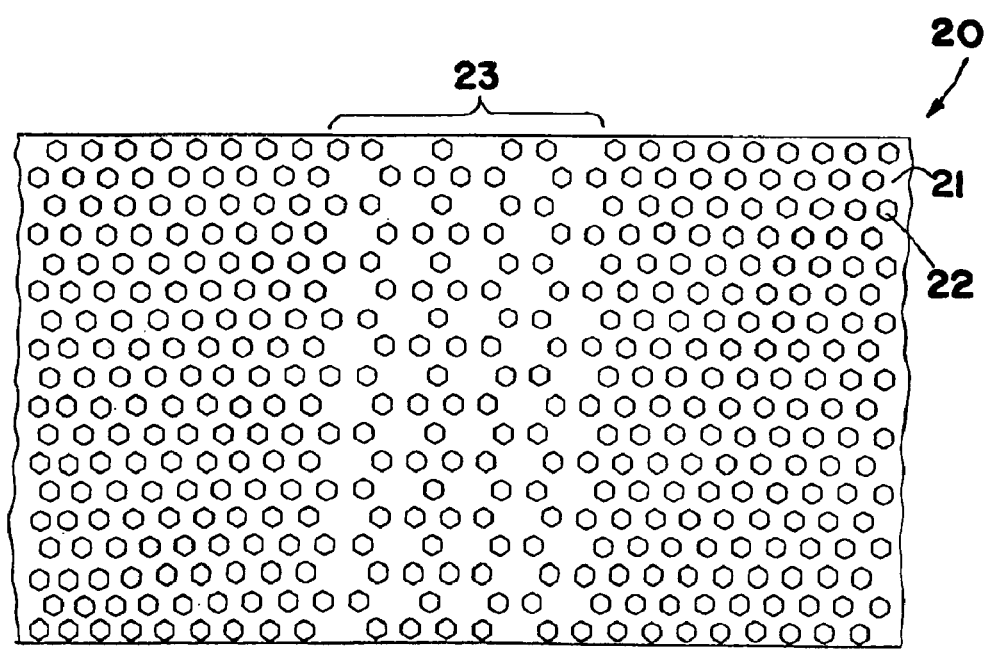
FIG. 2 is a top view of the backing layer and the patterned adhesive.

As stated above, suitable techniques to apply the adhesive in this discontinuous pattern include gravure coating, spray coating, melt blowing, flexographic printing such as offset flexographic printing or screen printing of adhesives. An added benefit of the printing techniques is the potential to design areas of concentrated adhesive for particular effects. For example, more adhesive could be applied only in the portion of the bandage that receives the padstock to aid in adherence of the padstock to the backing material. This embodiment is further illustrated in FIG. 2. Article 20 has adhesive layer 21 and adhesive free areas 22. In region 23, there is a higher level of adhesive to provide better adhesion of the wound covering layer.

The adhesive of the present medical bandage or tape may be any medical grade adhesive. The medical adhesives include suitable acrylic based pressure sensitive adhesives (PSAs), suitable rubber based pressure sensitive adhesives and suitable silicone pressure sensitive adhesives.

Useful rubber based PSAs include those taught in U.S. Pat. No. 5,705,551 (Sasaki et al.) and in U.S. Pat. No. 4,080,348 (Korpman), the disclosures of which are hereby incorporated by reference. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

A particularly useful rubber based adhesive is that which has a thermoplastic elastomeric component and a resin component. The thermoplastic elastomeric component contains about 55–85 parts of a simple A-B block copolymer wherein the A-blocks are derived from styrene homologs and the B-blocks are derived from isoprene, and about 15–45 parts of a linear or radical A-B-A block copolymer wherein the A-blocks are derived from styrene or styrene homologs and the B-blocks are derived from conjugated dienes or lower alkenes, the A-blocks in the A-B block copolymer constituting about 10–18 percent by weight of the A-B copolymer and the total A-B and A-B-A copolymers containing about 20 percent or less styrene. The resin component consists of essentially of tackifier resins for the elastomeric component. In general any compatible conventional tackifier resin or mixture of such resins may be used. These include hydrocarbon resins, rosin and rosin derivatives, polyterpenes and other tackifiers. The adhesive composition contains about 20–300 parts of the resin component per one hundred parts by weight of the thermoplastic elastomeric component. One such rubber based adhesive is commercially available from Ato Findley under the trade name HM3210.

Useful acrylic based PSAs include those taught in U.S. Pat. No. 5,947,917 (Carte), and U.S. Pat. No. 5,164,444 (Bernard, acrylic emulsion), U.S. Pat. No. 5,623,011 (Bernard, tackified acrylic emulsion). It can also be radiation curable mixture of monomers with initiators and other ingredients such as those taught in U.S. Pat. No. 5,232,958 (Ang, UV cured acrylic) and U.S. Pat. No. 5,232,958 (Mallya et al, EB cured). The disclosures of these patents and the pending application as they relate to acrylic adhesives are hereby incorporated by reference.

It is contemplated that any acrylic based polymer capable of forming an adhesive layer with sufficient tack to adhere to the facestock, the release liner or to a substrate, and with acceptable adhesion to skin, may function in the present invention. In certain embodiments, the acrylic polymers for the pressure-sensitive adhesive layers include those formed from polymerization of at least one alkyl acrylate monomer or methacrylate, an unsaturated carboxylic acid and optionally a vinyl lactam. Examples of suitable alkyl acrylate or methacrylate esters include, but are not limited to, butyl acrylate, ethyl acrylate, 2-ethylhexyl acrylate, isooctyl acrylate, isononyl acrylate, isodecyl acrylate, methyl acrylate, methylbutyl acrylate, 4-methyl-2-pentyl acrylate, sec-butyl acrylate, ethyl methacrylate, isodecyl methacrylate, methyl methacrylate, and the like, and mixtures thereof. Examples of suitable ethylenically unsaturated carboxylic acids include, but are not limited to, acrylic acid, methacrylic acid, fumaric acid, itaconic acid, and the like, and mixtures thereof. A preferred ethylenically unsaturated carboxylic acid monomer is acrylic acid. Examples of suitable vinyl lactams include, but are not limited to, N-vinyl caprolactam, 1-vinyl-2-piperidone, 1-vinyl-5-methyl-2-pyrrolidone, vinyl pyrrolidone, and the like, and mixtures thereof.

The adhesive may also include a tackifier. Tackifiers, are generally hydrocarbon resins, wood resins, rosins, rosin derivatives, and the like. It is contemplated that any tackifier known by those of skill in the art to be compatible with elastomeric polymer compositions may be used with the present embodiment of the invention. One such tackifier, found to be useful is Wingtak 10, a synthetic polyterpene resin that is liquid at room temperature, and sold by the Goodyear Tire and Rubber Company of Akron, Ohio. Wingtak 95 is a synthetic tackifier resin also available from Goodyear that comprises predominantly a polymer derived from piperylene and isoprene. Other suitable tackifying additives may include Escorez 1310, an aliphatic hydrocarbon resin, and Escorez 2596, a $C_5$–$C_9$ (aromatic modified aliphatic) resin, both manufactured by Exxon of Irving, Tex. Of course, as can be appreciated by those of skill in the art, a variety of different tackifying additives may be used to practice the present invention.

In addition to the tackifiers other additions may be included in the PSAs to impart desired properties. For example, plasticizers may be included and they are known to decrease the glass transition temperature of an adhesive composition containing elastomeric polymers. An example of a useful plasticizer is Shellflex 371, a naphthenic processing oil available from Shell Oil Company of Houston, Tex. Antioxidants also may be included on the adhesive compositions. Suitable antioxidants include Irgafos 168 and Irganox 565 available from Ciba-Geigy, Hawthorne, N.Y. Cutting agents such as waxes and surfactants also may be included in the adhesives.

Other optional materials which may be added to the adhesive layer in minor amounts (typically less than about 25% by weight of the elastomeric phase) include pH controllers, medicaments, bactericides, growth factors, wound healing components such as collagen, antioxidants, deodorants, perfumes, antimicrobials and fungicides.

Useful silicone pressure sensitive adhesives include those commercially available from Dow Corning Corp., Medical Products and those available from General Electric. Examples of silicone adhesives available from Dow Corning include those sold under the trade names BIO-PSA X7-3027, BIO-PSA X7-4919, BIO-PSA X7-2685, BIO-PSA X7-3122 and BIO-PSA X7-4502. Additional examples of silicone pressure sensitive adhesives useful in the present invention are described in U.S. Pat. Nos. 4,591,622, 4,584, 355, 4,585,836 and 4,655,767, incorporated herein by reference.

The adhesive article may be further described by reference to the accompanying drawings. FIG. 1 has adhesive article 10 with the backing layer containing adhesive layer 11 and adhesive free area 12. The pattern may be prepared by any means know to those in the art. The pattern could be formed by spraying the pressure sensitive adhesive or by melt blowing the pressure sensitive adhesive. The pattern could be formed by printing the adhesive. The printing may be any means that can for the pattern. Examples of useful printing means include gravure, lithographic, screen, or flexographic printing.

Figure 3:
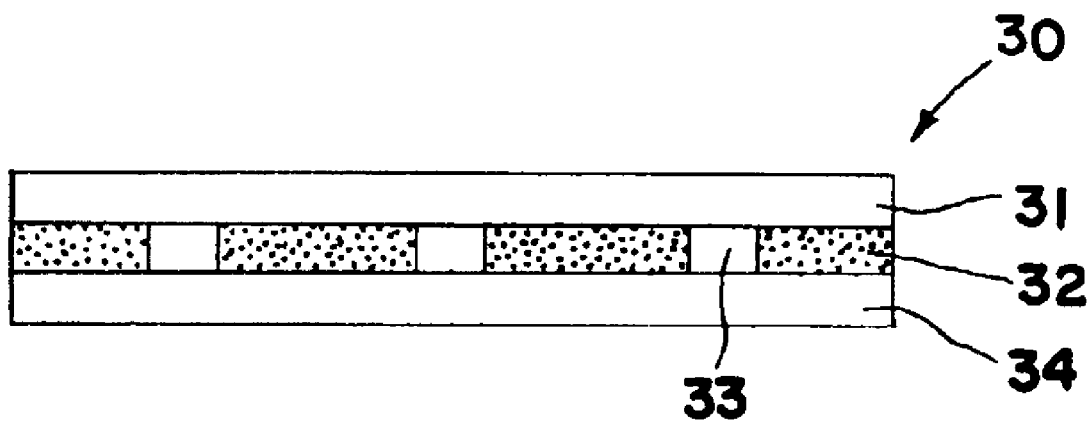
FIG. 3 is a cross sectional view of the adhesive article.

FIG. 3 is a cross section of an adhesive article. Article 30, has backing layer 31 which is adhered to adhesive 32 which has a pattern including adhesive-free areas 33. The adhesive 32 in turn is releasably adhered to release liner 32.

Figure 4:
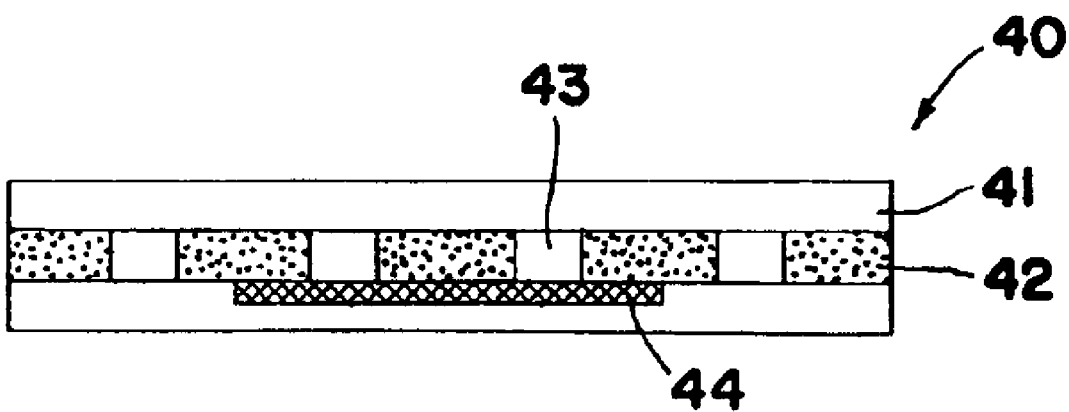
FIG. 4 is a cross sectional area of the adhesive article with the wound covering layer.

FIG. 4 illustrates an adhesive article with a wound covering layer. Article 40 has backing layer 41 that is adhered to patterned adhesive 42, including adhesive-free areas 43. The adhesive in turn is adhered, in part and releasably to release liner 45 and also, in part, to wound covering layer 44. It should be noted that the wound covering layer and the release liner may also be in contact. The wound covering layer may be any of those know in the art. These include absorbent materials such as fiber containing webs, gauze, etc. The fiber containing webs may be those made from rayon and polypropylene. For example, fiber containing webs include those with 70% rayon and 30% polypropylene and 50% rayon and 50% polypropylene. The wound covering layer of FIG. 4 covers a portion of the adhesive article. The article may be in the form of strips or rectangular bandages or island bandages.

When the adhesive article is used as a tape, then a release coating is placed on the second surface of the backing layer. The release coating may be any of those know in the art. These include sprayed silicone release coating. The release coating prevents the adhesion of the adhesive layer to the second surface of the backing layer.

EXAMPLES

The invention will be described in greater detail by the following examples.

Examples 1A–1C

Hot melt rubber based pressure sensitive adhesive, HM3210 from Ato Findley, was applied in a "honey comb" pattern onto a siliconized release liner by offset flexographic printing. The pattern was formed so that the adhesive covered 85–90% of the surface area of the release liner, with the remaining 10–15% of the surface area being free of adhesive. The coat weight of the adhesive is 40 grams per square meter (gsm). The adhesive coated liner is then laminated to a 3.3 mil apertured polyolefin film, X6989 from Tredegar Film Products. Rolls of the laminate material are then converted via a die cutting process in which the absorbent pad and finger tabs are applied, and the material cut to form the adhesive bandage strips.

Example 2

Adhesive strips are prepared substantially in accordance with Example 1, except that the hot melt rubber based PSA was applied to the release liner by spray coating the adhesive onto the release liner in a pattern so that the adhesive covered 85–90% of the surface area of the release liner and the coat weight was 40 gsm. The adhesive coated liner was then laminated to the apertured polyolefin film.

Example 3

Adhesive strips are prepared substantially in accordance with Example 1, except that the hot melt rubber based PSA was applied to the release liner by screen printing the adhesive onto the release liner in a pattern so that the adhesive covered 85–90% of the surface area of the release liner and the coat weight was 40 gsm. The adhesive coated liner was then laminated to the apertured polyolefin film.

Example 4

Adhesive strips are prepared substantially in accordance with Example 1, except that the hot melt rubber based PSA was applied to the release liner by gravure printing the adhesive onto the release liner in a pattern so that the adhesive covered 85–90% of the surface area of the release liner and the coat weight was 40 gsm. The adhesive coated liner was then laminated to the apertured polyolefin film.

Example 5

Adhesive strips are prepared substantially in accordance with Example 1, except that the hot melt rubber based PSA was applied to the release liner by flexographic printing the adhesive onto the release liner in a pattern so that the adhesive covered 85–90% of the surface area of the release liner and the coat weight was 40 gsm. The adhesive coated liner was then laminated to the apertured polyolefin film.

Example 6

Adhesive strips are prepared substantially in accordance with Example 1, except that the hot melt rubber based PSA was applied to the release liner by lithographcic printing the adhesive onto the release liner in a pattern so that the adhesive covered 85–90% of the surface area of the release liner and the coat weight was 40 gsm. The adhesive coated liner was then laminated to the apertured polyolefin film.

Comparative Example A

Adhesive strips are prepared substantially in accordance with Examples 1–6, except that the hot melt rubber based PSA was applied to the release liner by slot die caoting the adhesive onto the surface area of the release liner. With this method, the adhesive was extruded in a uniform thin layer onto the release liner. The coat weight of the adhesive was 35 gsm. The adhesive coated liner was then laminated to the apertured polyolefin film.

Comparative Example B

Adhesive bandage strips commercially available as BAND-AID Brand Sheer bandages were tested for comparative purposes. These bandages contain an acrylic emulsion adhesive coated onto a vinyl backing.

Samples of adhesive strips of the foregoing examples were tested for moisture vapor transmission rate (MVTR). Several samples were first subjected to aging conditions at higher temperature and relative humidity, and then evaluated using the foregoing tests. Table I sets forth the test results for the various samples.

TABLE 1

| Example | Sample | Condition | MVTR g/m$^2$/day |
|---------|--------|-----------|------------------|
| 1A | 1 | Initial | 10411 |
| | 2 | 4 wks 25 C/60 RH | 9587.5 |
| | 3 | 4 wks 40 C/75 RH | 9476.5 |
| | 4 | 4 wks 50 C | 9248 |

TABLE 1-continued

| Example | Sample | Condition | MVTR g/m²/day |
|---|---|---|---|
| | 5 | 8 wks 40 C/75 RH | 11132 |
| | 6 | 8 wks 50 C | 10500.5 |
| | 7 | 13 wks 25 C/60 RH | 7966.1 |
| | 8 | 13 wks 40 C/75 RH | 8310.3 |
| | 9 | 13 wks 50 C | 8261.5 |
| 1B | 1 | Initial | 8484.5 |
| | 2 | 4 wks 25 C/60 RH | 8020.5 |
| | 3 | 4 wks 40 C/75 RH | 9465.5 |
| | 4 | 4 wks 50 C | 9463.5 |
| | 5 | 8 wks 40 C/75 RH | 9458.5 |
| | 6 | 8 wks 50 C | 9803.5 |
| | 7 | 13 wks 25 C/60 RH | 8886.8 |
| | 8 | 13 wks 40 C/75 RH | 32636.8 |
| | 9 | 13 wks 50 C | 35850.7 |
| 1C | 1 | Initial | 6883 |
| | 2 | 4 wks 25 C/60 RH | 775.6 |
| | 3 | 4 wks 40 C/75 RH | 898.7 |
| | 4 | 4 wks 50 C | 1013.2 |
| Comp. Ex. A | 1 | | 282.5 |
| | 2 | | 230 |
| | 3 | | 109 |
| | 4 | | 145 |
| | 5 | | 294.5 |
| | 6 | | 149 |
| Comp. Ex. B | 1 | Commercial product | 4740 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of forming an adhesive article comprising
(a) providing a release finer having an upper surface,
(b) applying a continuous pressure sensitive adhesive layer to define a pattern of discontinuous adhesive free areas and continuous areas of the pressure sensitive adhesive on the upper surface of said release liner, wherein the pattern is formed simultaneously with the applying of the adhesive layer and a total area of the adhesive-free areas of the upper surface of said release liner is less than 25% of a total surface area of said upper surface of said release liner covered by the pressure sensitive adhesive layer, and
(c) applying a backing layer to the pressure sensitive adhesive layer.

2. The method of claim 1 further comprising the step of adhering a wound contacting layer to a portion of the pressure sensitive adhesive layer.

3. The method of claim 1 wherein the pattern is formed with gravure printing, flexographic printing, screen printing or spraying.

4. The method of claim 1 wherein the pattern is formed by flexogruphic printing a honeycomb pattern.

5. A method of facilitating wound healing comprising the steps of
providing an adhesive article having:
at least one apertured polymeric backing layer having a first and second surface;
a continuous pressure sensitive adhesive layer adhered to the first surface of the backing layer in a pattern, wherein the pattern of the adhesive layer defines a plurality of adhesive free areas, the combined area of which is less than about 25% of the surface, and the backing layer first surface defines from 2 to about 15 apertures disposed per adhesive free area, and wherein the adhesive article has a moisture vapor transmission rate of greater than about 2000 g/m²/24 hour; and
a wound contacting layer adhered to the pressure sensitive adhesive; and covering the wound with the adhesive article.

6. The method as defined in claim 1, wherein the adhesive-free area is in a range of from about 5% up to 10% of the total surface area of said upper surface.

7. The method as defined in claim 6, wherein and the adhesive-free area is in a range of from about 5% to about 8% of the total surface area of said upper surface.

8. The method as defined in claim 1, wherein the backing layer has a moisture vaportransmission rate in a range of greater than about 5000 g/m²/24 hours.

9. The method as defined in claim 8, wherein the backing layer has a moisture vapor transmission rate in a range of greater than about 7000 g/m²/24 hours.

10. The method as defined in claim 5, wherein the adhesive-free area is in a range of from about 5% up to 10% of the total surface area of said upper surface.

11. The method as defined in claim 10, wherein and the adhesive-free area is in a range of from about 5% to about 8% of the total surface area of said upper surface.

12. The method as defined in claim 5, wherein the backing layer has a moisture vaportransmission rate in a range of greater than about 5000 g/m²/24 hours.

13. The method as defined in claim 12, wherein the backing layer has a moisture vapor transmission rate in a range of greater than about 7000 g/m²/24 hours.

14. A method of forming an adhesive article, comprising:
providing a release liner having a surface;
applying a continuous pressure sensitive adhesive layer to the release liner surface, the pressure sensitive adhesive layer having a plurality of discontinuous adhesive free areas that define a pattern, wherein the pattern is formed simultaneously with the applying of the adhesive layer and a total area of the plurality of discontinuous adhesive-free areas is less than 25% of a total surface area of the release liner surface; and
applying an apertured backing layer to a surface of the pressure sensitive adhesive layer that is opposite the release liner, and wherein the backing layer defines from 2 to 15 apertures per adhesive free area.

15. The method as defined in claim 14, wherein the total area of the discontinuous adhesive free areas is in a range of from about 5% up to 10% of the total surface area of the release liner surface.

16. The method as defined in claim 15, wherein the total area of the discontinuous adhesive free areas is in a range of from about 5% to about 8% of the total surface area of the release finer surface.

17. The method as defined in claim 14, wherein the backing layer has a moisture vaportransmission rate in a range of greater than about 5000 g/m²/24 hours.

18. The method as defined in claim 17, wherein the backing layer has a moisture vapor transmission rate in a range of greater than about 7000 g/m²/24 hours.

19. The method as defined in claim 14, further comprising adhering a wound contacting layer to at least a portion of the pressure sensitive adhesive layer.

20. The method as defined in claim 14, further comprising adhering a wound contacting layer to at least a portion of the pressure sensitive adhesive layer, and wherein the total area of the discontinuous adhesive free areas is in a range of from about 5% to about 8% of the total surface area of the release liner surface, the backing layer has a moisture vapor transmission rate in a range of greater than about 7000 g/m²/24 hours, and the backing layer comprises a woven synthetic fabric or a knitted synthetic fabric, the pattern defines a plurality of smooth sine wave or of triangular waves, end the pressure sensitive adhesive is applied by melt blowing or by slot die coating.

* * * * *

UNITED STATES PATENT AND TRADEMARK OFFICE
CERTIFICATE OF CORRECTION

PATENT NO. : 6,953,602 B2  Page 1 of 1
DATED : October 11, 2005
INVENTOR(S) : Carte et al.

It is certified that error appears in the above-identified patent and that said Letters Patent is hereby corrected as shown below:

Column 8,
Line 37, replace "die caoting the" with -- die coating the --.

Column 9,
Line 50, replace "release finer having" with -- release liner having --.

Column 10,
Line 2, replace "flexogruphic printing" with -- flexographic printing --.
Lines 27, 38 and 66, replace "moisture vaportransmission rate" with -- moisture vapor transmission rate --.
Line 63, replace "release finer surface" with -- release liner surface --.

Signed and Sealed this

Third Day of January, 2006

JON W. DUDAS
*Director of the United States Patent and Trademark Office*